(12) United States Patent
Profio et al.

(10) Patent No.: US 9,514,275 B2
(45) Date of Patent: Dec. 6, 2016

(54) DIAGNOSTIC IMAGING SIMPLIFIED USER INTERFACE METHODS AND APPARATUS

(75) Inventors: Mark Vincent Profio, Elm Grove, WI (US); Sang Wook Lee, Brookfield, WI (US); David Alan Littlejohn, Wales, WI (US); Scott Wayne Zimmerman, Pewaukee, WI (US); Holly Ann McDaniel, Waukesha, WI (US); Susan Martignetti Stuebe, Whitefish Bay, WI (US); Patrick Michael Virtue, Waukesha, WI (US); Scott William Robinson, Bayside, WI (US); Ann Christine Hole, Greenville, OH (US); Christopher James Proctor, Mukwonago, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 2760 days.

(21) Appl. No.: 11/375,187

(22) Filed: Mar. 13, 2006

(65) Prior Publication Data

US 2007/0214017 A1 Sep. 13, 2007

(51) Int. Cl.
*G01C 21/32* (2006.01)
*G06F 19/00* (2011.01)
*A61B 6/00* (2006.01)
*G06Q 50/24* (2012.01)

(52) U.S. Cl.
CPC ........... *G06F 19/3406* (2013.01); *A61B 6/465* (2013.01); *A61B 6/467* (2013.01); *A61B 6/566* (2013.01); *G06F 19/321* (2013.01); *G06Q 50/24* (2013.01); *A61B 6/468* (2013.01); *A61B 6/469* (2013.01)

(58) Field of Classification Search
CPC ............................... G06F 19/00; G06Q 10/00
USPC ..................................................... 705/2, 3, 4
See application file for complete search history.

(56) References Cited

U.S. PATENT DOCUMENTS

| | | | |
|---|---|---|---|
| 4,835,690 A | 5/1989 | Gangarosa et al. | 364/413.13 |
| 5,247,661 A | 9/1993 | Hager et al. | 395/600 |
| 5,319,543 A | 6/1994 | Wilhelm | 364/401 |
| 5,321,520 A | 6/1994 | Inga et al. | 358/403 |
| 5,655,084 A | 8/1997 | Pinsky et al. | 395/203 |
| 5,715,823 A | 2/1998 | Wood et al. | 128/660.01 |
| 5,740,428 A | 4/1998 | Mortimore et al. | 395/615 |
| 5,745,901 A | 4/1998 | Entner et al. | 707/103 |
| 6,038,541 A | 3/2000 | Tokuda et al. | 705/8 |
| 6,041,306 A | 3/2000 | Du et al. | 705/8 |
| 6,047,081 A | 4/2000 | Groezinger et al. | 382/128 |
| 6,101,407 A | 8/2000 | Groezinger | 600/407 |
| 6,458,081 B1 | 10/2002 | Matsui et al. | 600/437 |
| 6,574,629 B1 | 6/2003 | Cooke, Jr. et al. | 707/10 |
| 6,603,494 B1 | 8/2003 | Banks et al. | 345/807 |

(Continued)

FOREIGN PATENT DOCUMENTS

| | | |
|---|---|---|
| JP | 10-031708 A | 2/1998 |
| JP | 2002-143095 A | 5/2002 |

(Continued)

*Primary Examiner* — Fonya Long
*Assistant Examiner* — Edward B Winston, III
(74) *Attorney, Agent, or Firm* — Fletcher Yoder, P.C.

(57) ABSTRACT

Apparatus includes an imaging system with a user interface, and a hospital radiological information system (RIS) coupled to the imaging system such that the user interface allows for bi-directional data transfer between the imaging system and the RIS.

7 Claims, 7 Drawing Sheets

(56) References Cited

U.S. PATENT DOCUMENTS

| | | | |
|---|---|---|---|
| 6,904,161 B1 | 6/2005 | Becker et al. | 382/128 |
| 2002/0143575 A1* | 10/2002 | Hansen et al. | 705/2 |
| 2003/0120516 A1* | 6/2003 | Perednia | 705/3 |
| 2003/0139944 A1* | 7/2003 | Carlsen et al. | 705/2 |
| 2004/0128164 A1* | 7/2004 | DeJarnette et al. | 705/2 |
| 2004/0169673 A1* | 9/2004 | Crampe et al. | 345/700 |
| 2004/0172291 A1* | 9/2004 | Knowlton | 705/2 |
| 2004/0236216 A1* | 11/2004 | Manjeshwar et al. | 600/436 |
| 2004/0267575 A1* | 12/2004 | Boing | 705/2 |
| 2005/0049179 A1* | 3/2005 | Davidson et al. | 705/3 |
| 2006/0031095 A1* | 2/2006 | Barth et al. | 705/2 |
| 2007/0150305 A1* | 6/2007 | Abraham-Fuchs et al. | 705/2 |

FOREIGN PATENT DOCUMENTS

| | | |
|---|---|---|
| JP | 2002-219122 A | 8/2002 |
| JP | 2003-233674 A | 8/2003 |
| JP | 2003-284694 A | 10/2003 |
| JP | 2003-290149 A | 10/2003 |
| JP | 2004-154560 A | 6/2004 |
| JP | 2004-171386 A | 6/2004 |
| JP | 2004-298267 A | 10/2004 |
| JP | 2004-337503 A | 12/2004 |
| JP | 2006-061278 A | 3/2006 |
| JP | 2007-278727 A | 10/2007 |

* cited by examiner

DIAGNOSTIC IMAGING SIMPLIFIED USER INTERFACE METHODS AND APPARATUS

BACKGROUND OF THE INVENTION

This invention relates generally to methods and apparatus for medical imaging, and more particularly to methods and apparatus that facilitate data acquisition and image review.

Imaging demand from medical imaging device continues to expand and Radiologist and Technologist shortages have resulted in an average medical imaging device user in being inundated with imaging data. This explosion of imaging data per person is problematic.

It would therefore be desirous to provide improved data handling and improved workflow in the medical imaging field.

BRIEF DESCRIPTION OF THE INVENTION

In one aspect, apparatus includes a imaging system with a user interface, and a hospital radiological information system (RIS) coupled to the imaging system such that the user interface allows for bi-directional data transfer between the imaging system and the RIS.

In another aspect, a method includes installing a user interface on multiple imaging systems of different imaging modalities.

In still another aspect, a method includes prospectively setting at least one of a window, an algorithm, and a projection based upon an organ interrogation system.

DETAILED DESCRIPTION OF THE INVENTION

Figure 1:
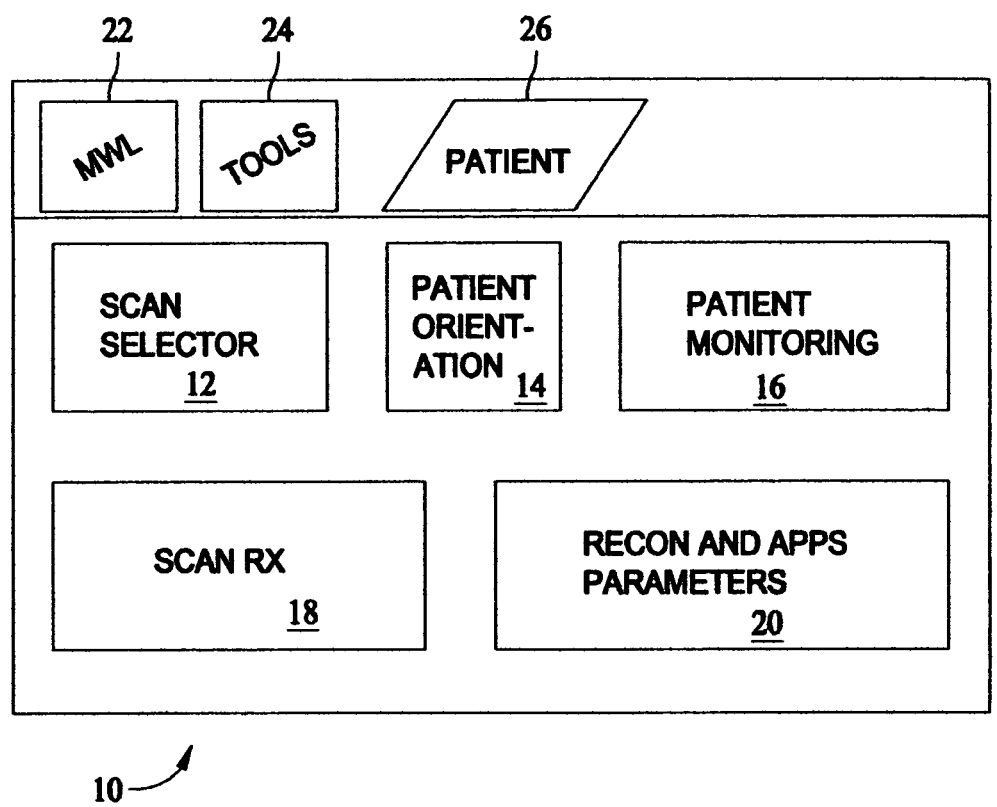
FIG. 1 illustrates a screen of the DISUI.

There are herein provided methods and apparatus useful for diagnostic imaging systems. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also, as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Herein described is a simplified user interface that prescribes, creates, and presents images ready for a radiologist to review. Technical effects include that this user interface addresses four primary workflow enablers, usability, enterprise interoperability, clinician flexibility/context specific Rx, and clinical performance. Usability means the user interface is learnable, efficient, memorable, error reducing, and a generally satisfying user interface. The interface includes a dashboard that tells the story of the exam and a "Procedure at a glance" that uncovers hidden information and removes clicks and checks. In one embodiment, organ-based protocols eliminate detailed parameter concerns for most exams. Enterprise interoperability means the scanner can retrieve data from a hospital Radiological Information System (RIS). The retrieved data includes lab values, patient location, and patient history for structured report text pages. The user interface allows information to be sent both to the RIS from the scanner and from the RIS to the scanner. The user interface also provides, in one embodiment, the ability to edit and/or group procedure codes and communicates completion of the grouping and/or editing to the RIS. An Auto-transfer of images by image range or "named volume" is provided in one embodiment. Consistent presentation of images by preserving measurements, user annotations, and filters is provided in another embodiment. Structured reports for dose page, exam and series text page, and exam and/or protocol notes are provided in one embodiment. Clinician flexibility/Context specific Rx means prospectively setting configurable image and/or application layouts in combination with user controlled automatic start of applications. Prospectively setting windows, algorithms, and projections based upon an organ interrogation system is done in one embodiment. The organ interrogation system interrogates a user for which organ is to be scanned. All the above can be generated automatically and simultaneously as previously designed exam by exam in organ-based protocols. Clinical performance is reducing variance and improving consistency of imaging results exam to exam. "Mistake Proofing" with automated bolus timing is provided in one embodiment. Streamlined workflow is provided by real-time control of contrast injection from the scanner user interface in one embodiment. This removes potential errors of starting sequences from different control interfaces and offers the ability to program or auto-adjust injection sequences. This allows for using less contrast agent and improves a patient's experience.

The herein described interface is a simplified user interface (SUI) for Diagnostic Imaging (DI) (SUIDI, also herein referred to as a Diagnostic Imaging Simplified User Interface DISUI, and SUI, and all those acronyms are used interchangeable herein). The SUI generally provides users the ability to choose a patient for an exam, associate a patient exam with a desired diagnostic imaging protocol that specifies: scan, timing, contrast timing, reconstruction, image display and/or review, and image processing required to make images ready for Radiologist review. In different embodiments, the SUI provides a bi-directional interface to a Hospital RIS system. The SUI provides support for enterprise interoperability with the scanner retrieving RIS data such as, for example, but not limited to lab values, patient location, and patient history for structured report text pages.

The SUI provides the ability to edit and/or group procedure codes and then the SUI communicates completion of the editing or grouping to the RIS.

The SUI provides a means to select a patient for a DI exam. The SUI provides a means to associate a DI protocol with a patient exam. The SUI provides a means to create and/or edit and/or select organ-based protocols. The SUI provides a means to create various protocols providing desired ready for Radiologist read outcomes for specific exams. The SUI provides a means for consistent presentation of images by preserving measurements, user annotations, and filters. The SUI provides support for structured reports for dose page, exam and series text page, and exam and/or protocol notes.

The SUI is common across multiple DI modalities such as CT, PET, MRI, etc. This use of a single interface across different modalities allows technicians and other users to be easily cross-trained on the different modalities.

The SUI is learnable, efficient, memorable, error reducing, and generally satisfying to users. The SUI includes, in one embodiment, a dashboard that communicates effectively the "Procedure at a Glance" for a technologist to easily perform a quality assurance review.

The SUI specifies a scan, scan timing, contrast timing, reconstruction, image display/review, and provides an application based image processing requirement that makes images ready for Radiologist review.

The SUI automatically starts image processing applications in the background (application auto-launch), under a user's control for review. The SUI supports configurable image display/review layouts that users can create/edit and save. The SUI allows users to easily change Patient Exam contexts for multitasking workflow.

The SUI supports clinician flexibility/context specific Rx means prospectively setting configurable image/application layouts in combination with user controlled automatic start of applications. The SUI prospectively setting windows, algorithms, and projections is based upon an organ interrogation system. All of this being generated automatically and simultaneously as previously designed exam by exam in organ-based protocols.

The SUI supports X-ray dose reduction functionalities and supports a scanner interface for contrast management/injection. The SUI supports appropriate automation of manual contrast timing procedures. The SUI has graphical prescription capability. The SUI has retrospective prescription capability. The SUI has enhanced Graphical prescription from any diagnostic imaging DICOM image.

Diagnostic imaging specific elements include: Scan Prescription (Rx); Image Reconstruction and Image Review/Processing Applications Prescription (Rx); Image range prescription for output functions; Patient Monitoring; and Patient Orientation Prescription (Rx).

The Scan Prescription (Rx) includes; At A Glance/Quick Check parameters; Scan parameters; Timing parameters; and Contrast Management Rx.

The Image Reconstruction and Image Review/Processing Applications Prescription (Rx) elements include: Image reconstruction parameters; Image Review/Processing Applications Rx and parameters; Configurable display/review layouts; Customizable view port definitions; Application Auto-Launch; and Application controls.

The Image range prescription for output functions include: Network, Hard Copy Filming, Long-term storage image archive, and Exam Split. The SUI supports Patient Monitoring and Patient Orientation Prescription (Rx).

Common elements across diagnostic imaging modalities include:
1. High Level Desktop Navigation
   a. Access to other tools including
      i. Modality Work List
      ii. Scanner specific utilities
      iii. Image Management Browser and Applications
2. Session Management
3. Workflow Task Manager
4. Graphical Prescription Diagnostic imaging specific element definitions for Scan Prescription (Rx) include:
1. At A Glance/Quick Check parameters provide users the vital few technical parameters they need to check before each patient scan. These parameters can be adapted/changed for the specific procedure being performed. At A Glance/Quick Check parameters are part of a predefined protocol created by users to perform a desired procedure. At A Glance/Quick Check simplifies the user interface by removing seldom-changed parameters from the top-level entry screen presented to users. One representative set of At A Glance/Quick Check parameters for a routine CT Helical scan acquisition could include and not be limited to:
   a. Scannable range as delineated by number of images
   b. Start scan location
   c. End scan location
   d. mA technique to be applied during the scan
2. Scan parameters provide users all technical parameters to fully prescribe a scan acquisition. These parameters can be adapted/changed for the specific procedure being performed. Scan parameters are part of a predefined protocol created by users to perform a desired procedure. One representative set of Scan parameters for a routine CT Helical acquisition could include and not be limited to:
   a. Scannable range as delineated by number of images
   b. Scan type
   c. Start scan location
   d. End scan location
   e. Number of images to be created
   f. Table Speed
   g. Helical pitch
   h. Gantry tilt
   i. Scan field of view
   j. kV technique to be applied during the scan
   k. mA technique to be applied during the scan
   l. Patient Size Adjusted Noise Index
   m. Desired Noise Index
   n. Total X-Ray Exposure Time
3. Timing parameters provide users all technical parameters to fully prescribe timing for a scan acquisition. These parameters can be adapted/changed for the specific procedure being performed. Timing parameters are part of a predefined protocol created by users to perform a desired procedure. One representative set of Timing parameters for a routine CT Helical acquisition could include and not be limited to:
   a. Scannable range as delineated by number of images
   b. Total Exposure Time
   c. Prep Group Delay
   d. Inter-Scan Delay
   e. Breath Hold Time
   f. Breathe Time
   g. Auto-Voice Selection
   h. Auto-Scan Lights Selection
   i. Auto-Count-Down Timer
   j. CINE Scan Duration Time
4. Contrast Management prescription (Rx) provides users with a variety of options to control the delivery of contrast enhancing agents and/or radiopharmaceuticals. These choices can be adapted/changed for the specific procedure being performed. Contrast Management Rx is part of a predefined protocol created by users to perform a desired procedure. One set of representative Contrast Management selections and combinations could include and not be limited to:
a. Intravenous Contrast (IV) injection
b. Oral Contrast administration
c. Automated detection method of contrast enhancement peak point utilizing a feature called "Smart Prep"
d. Automated Timing Bolus method for achieving optimum contrast enhancement
e. Scanner based control and prescription of automated contrast injection for IV procedures Diagnostic imaging specific element definitions for Image Reconstruction and Image Review/Processing Applications Prescription (Rx) includes:

1. Image reconstruction parameters provide users all technical parameters to fully prescribe the method required to produce images from a scan acquisition. These parameters can be adapted/changed for the specific procedure being performed. Image reconstruction parameters are part of a predefined protocol created by users to perform a desired procedure. Multiple reconstructions, up to "N", can be specified from one volume of acquired scan data, each with a unique reconstruction prescription. One representative set of Image reconstruction parameters for a routine CT Helical acquisition could include and not be limited to:
   a. Scannable range as delineated by number of images
   b. Image Thickness in millimeters
   c. Image Interval in millimeters
   d. Right/Left Center in millimeters
   e. Anterior/Posterior Center in millimeters
   f. Reconstruction Type
   g. Matrix Size
   h. Image Thickness modifier
   i. Window Width and Window Level
   j. Reconstruction Filter
2. Image Review/Processing Applications selections and parameters provides users the capability to review and process images in a most efficient manner. These selections and parameters can be adapted/changed for the specific procedure being performed. These selections and parameters are part of a predefined protocol created by users to perform a desired procedure. Image Review/Processing Applications can be associated with a unique range of images in any reconstructed set of images. Image Review/Processing Applications can be associated with multiple reconstructed image sets.
   a. One representative set of Image Review/Processing Applications selections could include and not be limited to:
      1. Configurable Image review layout includes both the quantity and dimensions of one or more unique view ports. For example, an image review layout might include up to six 512 pixel by 512 pixel view ports.
      2. Customizable view port definitions, the ability to uniquely define the application associated with each view port. For example, one view port could be defined to display simple two-dimensional axial images. Another view port, in the same layout, could be defined to display a three dimensional volume in a coronal view, building as images are reconstructed. Another view port, in the same layout could be specified to display the output of an advanced image processing application.
      3. Selection of multiple unique image processing applications operating on a defined range of reconstructed images.
      4. Automated-Launch of Image Review/Processing Applications. On an application-by-application basis, and on a protocol-by-protocol basis within an application, definitions can be created for automatic activities that can be performed by Image Review/Processing Applications upon receipt or consumption of the specified image range. These activities can occur in the background so they are either complete or in-progress when users bring this application to the foreground.
      5. Specific Image Review/Processing controls are associated with each application, and with each protocol within the application.
   b. One representative set of Image Review/Processing Applications parameters could include and not be limited to:
      1. Scannable range as delineated by number of images
      2. Image Review/Processing Application selection
      3. Image Review/Processing Layout selection
      4. Image Review/Processing view port definitions
      5. Image Review/Processing Application protocol selection
      6. Series description for images created by Image Review/Processing Application
      7. Start location of image range that will be input to or consumed by the Image Range/Processing Application
      8. End location of Image range that will be input to or consumed by the Image Range/Processing Application
      9. Other Image Review/Processing specific parameters Image range prescription for output functions, associating a unique desired image range with one or more output functions including:
1. Network destinations
2. Hard Copy Filming
3. Long term storage image archive
4. Exam Split Image range prescription for output functions include selections and parameters that can be adapted/changed for the specific procedure being performed. These selections and parameters are part of a predefined protocol created by users to perform a desired procedure. As an example, one representative set of network selections and parameters could include and not be limited to:
1. Scannable range as delineated by number of images
2. Grey Scale Presentation State (GSPS), or "Presentation State", protocol
3. Up to "N" destination network host/hosts
4. . Network transfer method Patient Monitoring displays time varying parameters of the patient being imaged in both graphical and textual form. These may include one or more of the following specific element definitions including:
1. Vital sign, heart rate with EKG trace vs. time and real-time textual heart rate readout.
2. Vital sign, respiration rate trace vs. time and real-time textual respiration rate readout.

Patient Orientation Prescription (Rx) allows users to specify landmark location and desired patient orientation before scanning. These selections and parameters can be adapted/changed for the specific procedure being performed. These selections and parameters are part of a predefined protocol created by users to perform a desired procedure.

Common elements across diagnostic imaging modalities include:

1. High Level Desktop Navigation
   a. Access to other tools including
      i. Modality Work List which provides users access to an active patient list, associating patients with procedure codes and scanning/imaging protocols.
      ii. Scanner specific utilities which could include but not be limited to:
         1. Daily scanner preparation activities
         2. Scanner utilities
         3. Retrospective Image Reconstruction, creating additional image sets from previously acquired scan data.
         4. Scan Data and Reconstruction Management, reserving specific scan data and recovery from reconstruction errors.
         5. Protocol Management, reviewing, creating, and editing scanner/imaging protocols.
         6. Service tools, specialized software based tools for servicing a scanning system.
         7. On-line educational and tutorial help with scanner operation and control.
         8. Network access to the scanner's manufacturer for remote service and educational help.
         9. Access to a detailed scanner error log.
      iii. Image Management Browser and Applications, access to the patient image database on the scanner. Access to a suite of Image Review/Processing Applications that perform various operations on patient images.
2. Session Management provides users with the ability to keep available, via a shortcut method, multiple patient exams. Session Management allows users to easily switch session contexts and multi-task different operations on multiple patient exams.
3. Workflow Task Manager, provides users a visible controllable set of tasks that also communicate task status/completion within a scanner protocol. Users control scan tasks, image review/processing tasks, and automated-tasks. Scan tasks include selecting scans for processing, copying/repeating scans, defining new scans, re-ordering scans, and deleting scans. Image review/processing tasks include selecting tasks for foreground display, copying/repeating tasks, defining/adding new tasks, re-ordering tasks, pausing/resuming tasks, and deleting tasks. Automated tasks include image reconstruction, networking, hard copy filming, archiving, and exam splitting. Automated tasks status can be viewed, paused/resumed, new automated tasks defined/added, re-ordered, and deleted.
4. Graphical Prescription provides users with the ability to prescribe subsequent scans and image review/processing applications from any cross-reference image in the scanner image database. Graphical prescription will be available both prospectively and retrospectively. Graphical prescription provides multiple user selectable views including:
   a. Individual Scan—Reconstruction views for multiple prospective reconstructions.
   b. Auto-Reformat view for prescription of "direct" or automatic three-dimensional volume reformats in coronal, sagital, and oblique planes.
   c. Multiple additional views to associate an image range with a specific application.

Diagnostic Imaging Simplified User Interface Relationships to Imaging Chain

1. The DISUI system typically includes, but does not have to, two high definition LCD monitors. The left monitor is dedicated to patient and protocol selection and detailed Exam prescription (Rx). The right monitor is dedicated to image review and processing. The DISUI system is independent of monitor configuration and can support 1 through "N" monitors.
2. Users enter the system from a password protected HIPAA log in screen on the left monitor.
3. Successful log in transitions users to a Modality Work List (MWL) screen. Here users may update/refresh the screen and then choose the appropriate patient for a diagnostic imaging exam.
4. Patient selection from MWL transitions users to the top level View/Edit prescription (Rx) screen. At this point, in the patient exam, users can either perform a quality assurance review of the protocol details for the selected procedure or detailed parameter edits. Dashboard user interface elements tell the story of the exam. This exam dashboard includes:
   a. At A Glance/Quick Check parameters
   b. Scan parameters
   c. Timing parameters
   d. Contrast Management Rx
   e. Image Reconstruction and Image Review/Processing Applications Prescription (Rx)
      1. Image reconstruction parameters
      2. Image Review/Processing Applications Rx and parameters
      3. Configurable display/review layouts
      4. Customizable view port definitions
      5. Application Auto-Launch
      6. Application controls
   f. Image range prescription for output functions including:
      1. Network
      2. Hard Copy Filming
      3. Long term storage image archive
      4. Exam Split
   g. Patient Monitoring
   h. Patient Orientation Prescription (Rx). Users review the Rx and in 80 to 90% of all cases are satisfied enough to "Confirm" the first scan series. In CT exams, this is typically a "Scout" scan. CT Scout scans provide images from which adjustments can be made to tune scan series scannable volume/s for individual anatomical differences.
5. The right monitor is dedicated to image review and processing. It also is enabled with the knowledge of a patient exam or session context. This allows users to decouple prescription on the left monitor from image review/processing on the right monitor. Users may choose the patient exam/session context they wish to work on. This enables "multi-patient exam/session multi-tasking". While the present patient is being prepped and perhaps scanned by one technologist in the scan room, a second technologist can be completing the image review/processing for another perhaps previous patient. Users choose their desired patient exam/session context and then have full control over the image review/processing and auto-tasks (reconstruction, networking, hard copy filming, and exam split) associated with that patient exam/session. This control includes pausing and resuming tasks, adding tasks, and deleting tasks. It further includes full suites of detailed controls tied to the image review/processing tasks being performed. Users may choose, at this point in the exam, to switch the exam/session context to the present exam/session and review the scout images as they are reconstructed and displayed on the right monitor.

6. Both monitors provide users with desktop management capability. Desktop management allows users to navigate at a high level to wholly different functional areas including:
   a. Modality Work List
   b. Scanner specific utilities
   c. Image Management Browser
7. CT scanning protocols typically consist but are not limited to at least two scan series with the first scan series typically being a Scout scan series. With successful completion of the Scout scan/s users typically progress to the next scan series. On the left monitor is a Workflow Task Manager that allows users to select the next scan series in the overall patient procedure/protocol.
8. Selection of the next scan series from the workflow task manager transitions the left monitor to the view/edit Rx screen containing the exam dashboard uniquely defined for that scan series. The right monitor automatically transitions to a special prescription function screen called Graphical Prescription (Rx). Users may make specific adjustments in Graphical Rx to tune the scan acquisition for patient differences. In addition, dedicated graphical views for other image processing applications are also provided to help users dial in their Rx for individual patients. This graphical Rx activity occurs on the right monitor. Users once again can choose to quickly review the unique exam dashboard for this series on the left monitor and then confirm the scan acquisition or edit any or all parameters they desire to change. In 80-90% of all cases, the exam dashboard Rx should be correct requiring little or no editing beyond those graphical adjustments made on the right monitor.
9. Once a user confirms the next scan series, the right monitor transitions to an image review/processing presentation tuned specifically for this scan series.
10. Image range prescription for output functions including networking, hard copy filming, archiving, and exam split are available to users in every reconstruction for every scan series within a patient exam/session.
11. Patient monitoring is available in Cardiac CT studies and perhaps in others as well at every point in the patient exam. Patient Monitoring displays time varying parameters of the patient being imaged in both graphical and textual form. These may include one or more of the following specific element definitions including:
    a. Vital sign, heart rate with EKG trace vs. time and real-time textual heart rate readout.
    b. Vital sign, respiration rate trace vs. time and real-time textual respiration rate readout.
12. Patient orientation can be reviewed/edited at any point in the patient exam. Patient Orientation Prescription (Rx) allows users to specify landmark location and desired patient orientation before scanning. These selections and parameters can be adapted/changed for the specific procedure being performed. These selections and parameters are part of a predefined protocol created by users to perform a desired procedure FIG. 1 illustrates a screen 10 of the DISUI where a user may select a scan selector option 12, a patient orientation option 14, a patient monitoring option 16, a scan Rx 18, and a reconstructions and applications parameters option 20. Additionally, screen 10 illustrates a Modality Work List tab 22, a tools tab 24 and a patient tab 26

Figure 2:
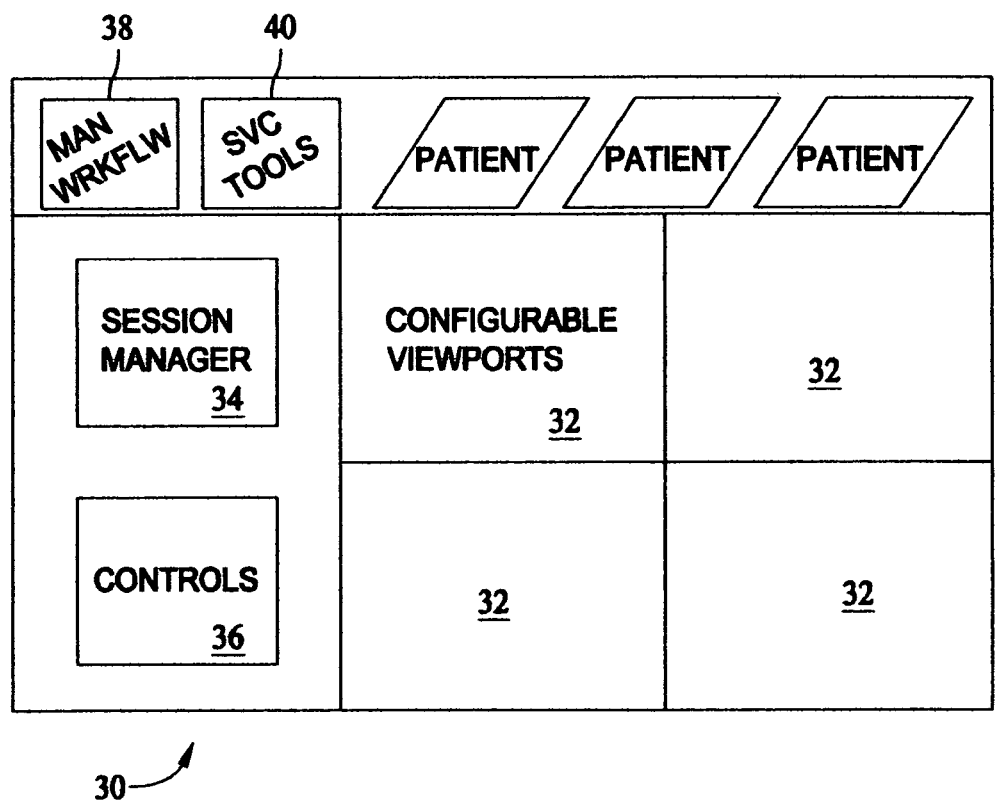
FIG. 2 illustrates a screen of the DISUI.

FIG. 2 illustrates a screen 30 of the DISUI with four configurable viewports 32, a session manager option 34, and a controls option 36. Screen 30 also shows a workflow manager tab 38 and a service tools tab 40.

Figure 3:
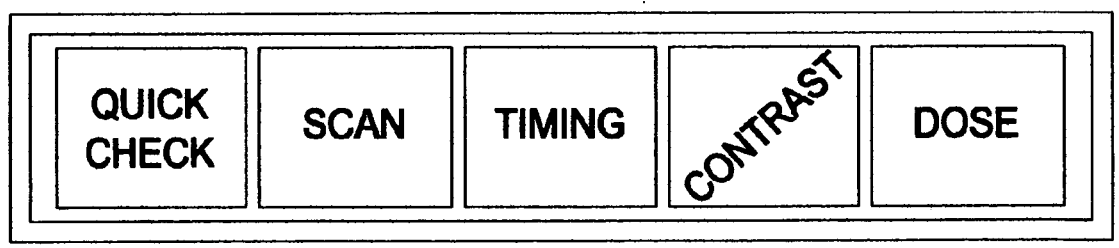
FIG. 3 illustrates a dashboard of the DISUI.

FIG. 3 shows a dashboard 50 of the DISUI that tells the story of the exam by setting forth the order of the different procedures and their descriptions. Note an Add button (A) and a Delete button (D) on bottom. In FIG. 3, the first procedure a Scout scan is in process (IP), and the user is able to pause the procedure. FIG. 3 also shows. a) At A Glance/Quick Check parameters, b) Scan parameters, c) Timing parameters, d) Contrast Management Rx and e) Image Acquisition parameters such as dose.

Figure 4A:
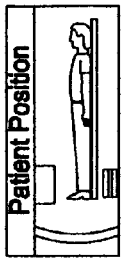
FIG. 4 illustrates a screen of the DISUI.
Figure 4B:
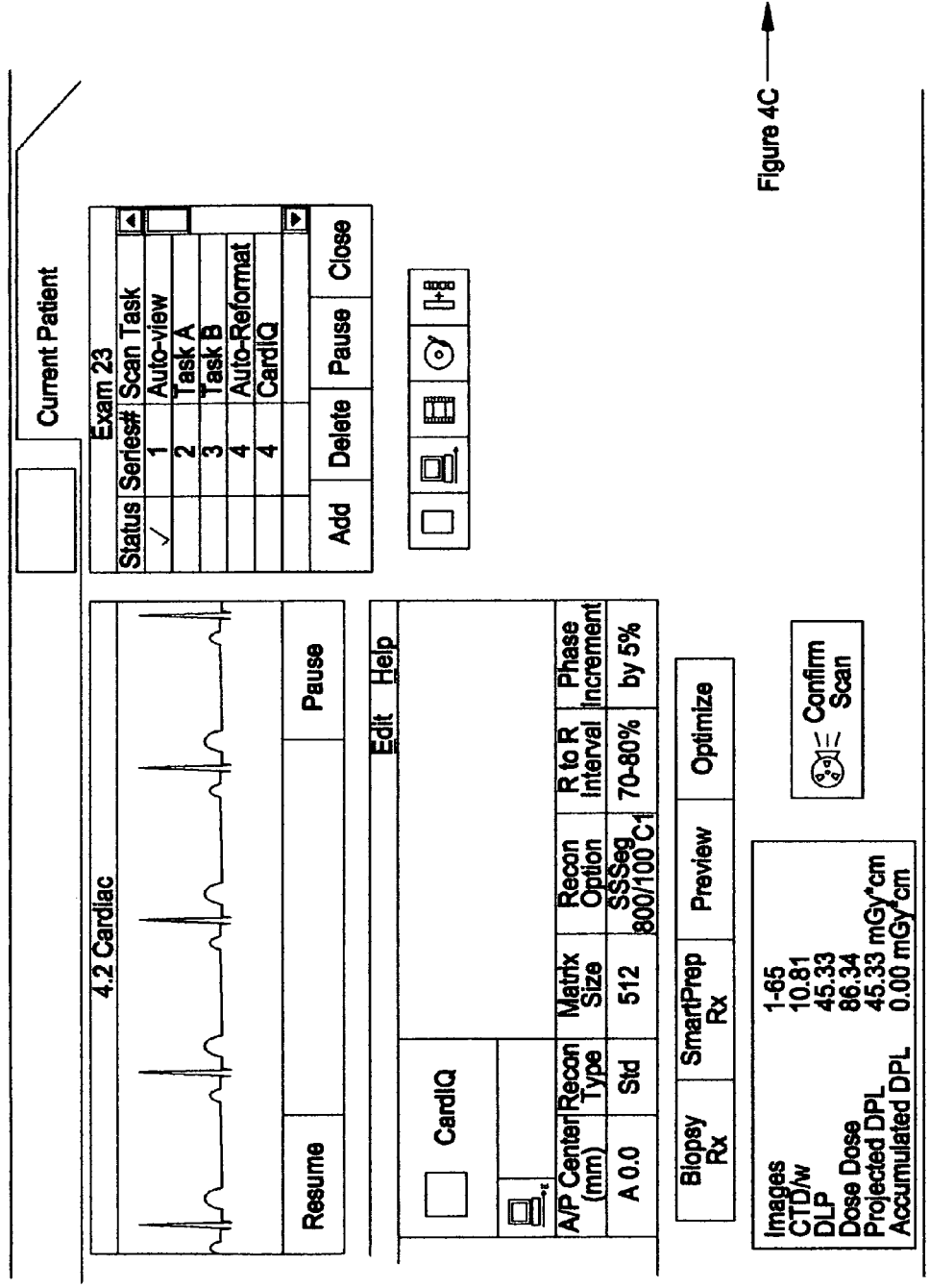
Figure 4C:
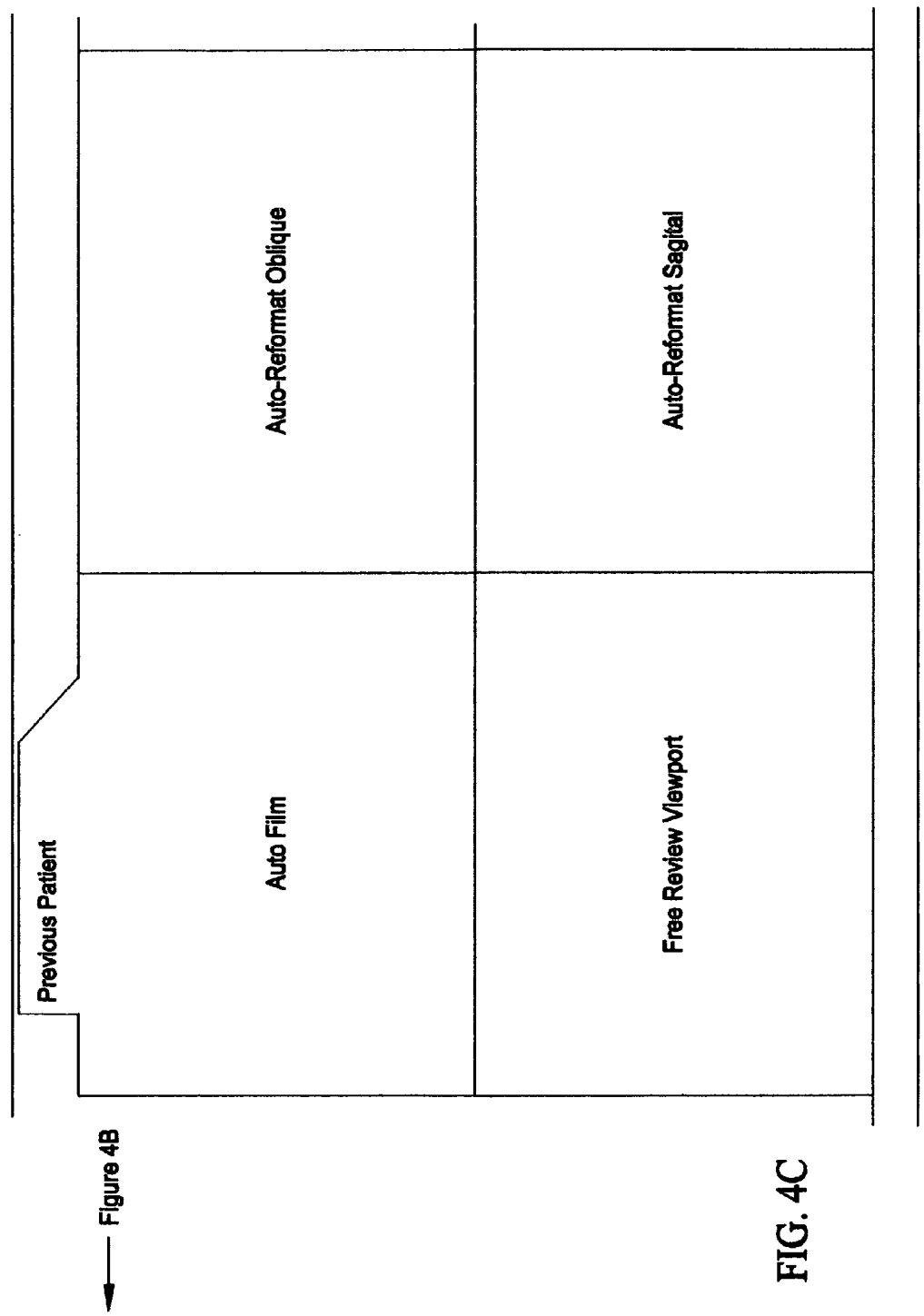

FIGS. 4a, 4b, and 4c (collectively called FIG. 4) is a screen shot of the DISUI wherein FIG. 4a is the left, 4b is the center and 4c is the right and is partially truncated on the right side as explained below. Starting with 4a, there is a current patient tab at the top. Beneath the current patient tab is a scan protocol area with an example 4.2 Cardiac protocol which includes a series of scans starting with a scout scan and then a helical localizer scan, followed by an axial scan with a timed bolus injection, and ending with a cardiac helical scan with parameters SSSeg, 0.625 mm slice thickness, and large SFOV (Scan Field of View). SSSeg stands for "Snapshot Segment" which is a special Cardiac Helical reconstruction algorithm. The algorithm is tuned to make optimal images at certain heart rate ranges for example 60 beats per minute to 90 beats per minute. As patient heart rate falls out of or exceeds a certain range we would recommend a different reconstruction algorithm to better match up with the patients real heart rate. The DISUI allows a user to repeat the series, to select a new protocol, and to save the protocol. The DISUI also includes a scan parameter area where the user can perform a quick check as explained above, can view scan parameters, timing parameters, select a contrast, add bolus information, and comments/notes. Below the scan parameter area is an optimize button, a SmartPrep button, a Priority Reconstruction button, and a one more button. "One More" is a shortcut prescription for 1 more scan beginning at the Rx'd End Location and then persisting for 1 revolution of the scanner gantry. So in a 40 mm scanner this button would scan an additional 40 mm (1 revolution) and reconstruct an image from this scan data. This is typically used to cover the scenario where a scan was a little short and needed to be lengthened to obtain proper patient coverage. Nearby is an End Scan button and a display of parameters, such as kV and mA for the x-ray tube voltage and amperage, exposure time, thickness, helical pitch, SFOV (Scan Field of View), auto voice, voice light, timer, DFOV (Displayed Field of View), rotation speed, and interval. Auto-Voice is a function that "plays" pre-recorded breathing instructions for the patient during the exam. "Lights" are special iconified lights in the scanner gantry that patients can see, the lights have special icons that indicate "hold your breath" or "breathe" this is provided for patients that are more visually oriented than verbally oriented. Returning to the top of FIG. 4a, there is a patient position area that allows the user to specify how the patient is positioned in the scanner, and to add a scan number. There is also a localizer button. Below the localizer button is a recon (i.e., reconstruction) parameters area that allows for exporting the parameters. Next to the reconstruction parameter area is an auto reformat area including options to export and save the auto reformat parameters such as a different DFOV then as originally displayed and any re-centering information both Right/Left and Anterior/Posterior, both in mm.

Referring now to FIG. 4b, at top is an EKG of graph with buttons to pause and resume the scan. The screen displays reconstruction type, matrix size, reconstruction options, R to R interval, and Phase Increment. Buttons include a Biopsy Rx button, a SmartPrep button, a Preview button, and an Optimize button. Information displayed include the number of images, a Ct dose weighted (CTDI/w), a Dose Length Product (DLP), a dose, a projected DLP, and an accumulated DLP. Nearby is a confirm scan button the user can press to confirm. There is a CardIQ tab a user may select to access a CardIQ Function Analysis tool, which is an application used to display cardiac CT images and semi-automatically or manually calculate left ventricular (LV) and right ventricular (RV) functional parameters. One embodiment includes a lung VCAR tab were VCAR means Volume computer-assisted reading. The application is optimized to perform assessment of cardiac function using multi-phase, multi-slice cardiac CT images. Toward the right side of FIG. 4b is an area that displays the current patient's name, and the scan tasks, series number, and statuses. Tasks may be added, deleted, paused, and closed. There is also a list of "image processing tasks" under the banner of "Exam 23". These are user selectable image review/processing tasks that map to the left screen application dashboard. So for example, the "Auto-Reformat" task maps to "Auto-Reformat" in the left screen dashboard. These tasks or applications are Rx'd on the left and execute and are user controlled on the right. Left Click selection of a task in this list causes it to "come forward" and be displayed to the user.

FIG. 4c illustrates the screen displays six viewports simultaneously. In addition to the four viewports shown in FIG. 4 as Auto Film, Auto-Reformat Oblique, free review viewport, Auto-Reformat Sagittal, there are two additional viewports which are truncated in FIG. 4c. The viewports shown truncated are Auto-Reformat Axial and Auto-Reformat Coronal.

Figure 5:
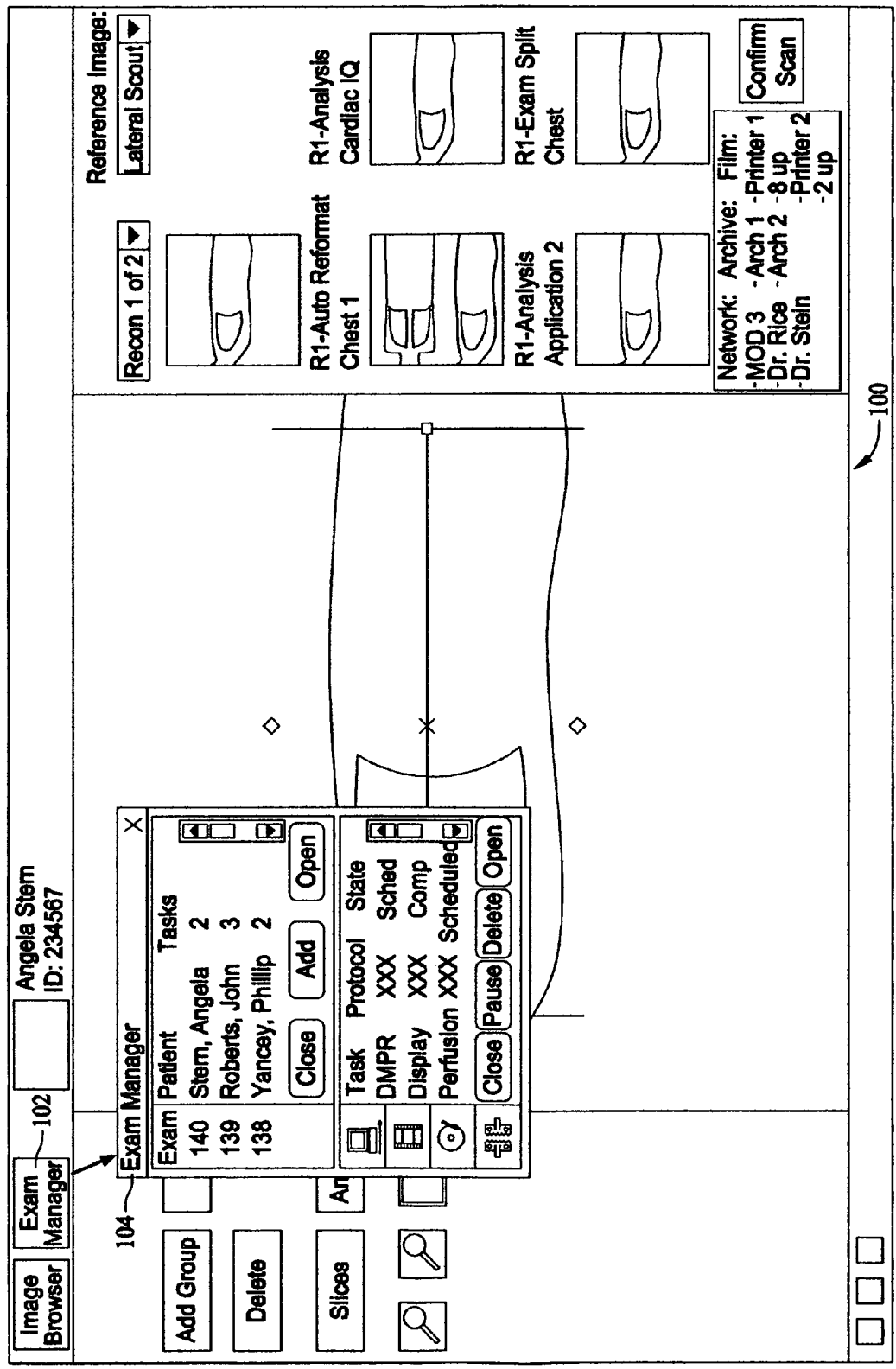
FIG. 5 illustrates a screen of the DISUI.

FIG. 5 illustrates a screen shot showing a centrally disposed main image section 100 wherein the user can select an area of interest as illustrated. Above the main image section 100, the patients name and ID number are displayed. An exam manager button 102 when selected displays an exam manager window 104 showing the exam number, the patient names, and number of tasks for each exam. Exams can be added, closed, and opened. Also displayed are tasks, protocols, and states of the tasks. Tasks can be deleted, paused, closed, and opened. On the right of FIG. 5 are a plurality of images including a recon 1 (R1) of two which is displayed with a drop down to move to the second recon. A reference image can also be displayed such as the scout image that was used to select recon 1. Note other images include a Auto Reformat image Chest 1, an Analysis Cardiac IQ image, an Analysis Application 2 image, and an Exam Split Chest image. Each image can be selected to be displayed in main image section 100. FIG. 5 also illustrates options to send the data over a network to particular Doctors or other clinicians, or to another location. The data can be archived or sent to film. In the film example, the user can both select the particular printer to send to and the layout of the images.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method for diagnostic imaging implementing an imaging system that includes a user interface, the method comprising:

accessing a radiological information system (RIS) from the user interface of the imaging system, the RIS having stored thereon subject data on a plurality of subjects;

selecting from the user interface a subject to be imaged from the plurality of subjects in the RIS;

selecting from the user interface an organ-based protocol for a diagnostic imaging scan to be performed on the selected subject;

displaying on the user interface a plurality of diagnostic imaging specific elements for the selected organ-based protocol;

providing for user editing of the plurality of diagnostic imaging specific elements on the user interface;

performing a diagnostic imaging scan on the selected subject based on the selected organ-based protocol and any user edits of the plurality of diagnostic imaging specific elements;

displaying on the user interface an image reconstructed from image data acquired from the diagnostic imaging scan; and communicating completion of the scan to the RIS.

2. The method of claim 1 wherein displaying the plurality of diagnostic imaging specific elements comprises displaying the plurality of diagnostic imaging specific elements on a first display monitor; and wherein displaying the reconstructed image comprises displaying the reconstructed image on a second display monitor.

3. The method of claim 2 further comprising displaying on the second display monitor a previously acquired image from the selected subject or another subject, the previously acquired image being displayed during performance of the diagnostic imaging scan on the selected subject and prior to display of the reconstructed image.

4. The method of claim 1 further comprising:

selecting from the user interface an organ-based protocol for a second diagnostic imaging scan to be performed on the selected subject upon completion of the first scan; and displaying a plurality of diagnostic imaging specific elements for the selected organ-based protocol for the second diagnostic imaging scan.

5. The method of claim 4 further comprising displaying a graphical prescription for the selected organ-based protocol for the second diagnostic imaging scan, the graphical prescription configured to allow for multiple user selectable views of a reconstructed image.

6. The method of claim 1 wherein the plurality of diagnostic imaging specific elements includes a scan prescription, an image reconstruction and review prescription, and an image range prescription.

7. The method of claim 6 wherein the scan prescription includes predefined scan protocol, technical scan parameters, scan timing parameters, and contrast management prescription; and wherein the image reconstruction and review prescription includes image reconstruction parameters, image review parameters, a configurable display layout, image view port settings, and background auto image processing and review.

* * * * *